(12) United States Patent
Berube et al.

(10) Patent No.: US 6,623,492 B1
(45) Date of Patent: Sep. 23, 2003

(54) TISSUE FASTENER

(75) Inventors: Rod Berube, North Attleboro, MA (US); Paul A. Torrie, Marblehead, MA (US); Steve Ek, Bolton, MA (US); John Lipchitz, Tewksbury, MA (US)

(73) Assignee: Smith & Nephew, Inc., Andover, MA (US)

( * ) Notice: Subject to any disclaimer, the term of this patent is extended or adjusted under 35 U.S.C. 154(b) by 0 days.

(21) Appl. No.: 09/490,525

(22) Filed: Jan. 25, 2000

(51) Int. Cl.$^7$ ................................................ A61B 17/08
(52) U.S. Cl. ..................... 606/151; 606/72; 606/77; 411/2
(58) Field of Search ................... 606/151, 72, 73, 606/75, 76, 77, 104, 213, 232; 411/5, 6, 456, 906, 907, 908, 392, 916, 2; 623/13.11, 13.15, 13.18, 13.19, 13.2; 24/298, 300, 47

(56) References Cited

U.S. PATENT DOCUMENTS

| | | |
|---|---|---|
| 3,664,345 A | 5/1972 | Dabbs et al. |
| 3,695,271 A | 10/1972 | Chodrow |
| 3,716,058 A | 2/1973 | Tanner, Jr. |
| 3,953,896 A | 5/1976 | Treace |
| 3,976,079 A | 8/1976 | Samuels et al. |
| 4,287,807 A | 9/1981 | Pacharis et al. |
| 4,409,974 A * | 10/1983 | Freedland .................... 606/72 |
| 4,532,926 A | 8/1985 | O'Holla |
| 4,532,927 A | 8/1985 | Miksza, Jr. |
| 4,534,350 A | 8/1985 | Golden et al. |
| 4,548,202 A | 10/1985 | Duncan |
| 4,621,639 A | 11/1986 | Transue et al. |
| 4,627,437 A | 12/1986 | Bedi et al. |
| 4,632,100 A | 12/1986 | Somers et al. |
| 4,669,473 A | 6/1987 | Richards et al. |
| 4,693,248 A | 9/1987 | Failla |
| 4,708,132 A | 11/1987 | Silvestrini |

(List continued on next page.)

FOREIGN PATENT DOCUMENTS

| | | |
|---|---|---|
| EP | 0232049 | 8/1987 |
| EP | 0464480 | 1/1992 |
| WO | 85/03857 | 8/1985 |
| WO | 89/01767 | 3/1989 |
| WO | WO98/22047 | 5/1998 |
| WO | WO99/01071 | 1/1999 |
| WO | WO99/01084 | 1/1999 |

OTHER PUBLICATIONS

Bio Stinger, "Bio–Absorbable Meniscal Fixation," Surgical Technique, 1998 Linvatec Corporation.
"Meniscus Repair," Clearfix Meniscal Screw, 1998 Innovasive Devices, Inc.
Mitek Meniscal Repair System, "A New Curve in Tissue Repair," Mitek Products, a Division of Ethicon, Inc., 1998.
"Clearfix Meniscal Dart," "Clearfix Meniscal Screw," Product Sheet (undated).

*Primary Examiner*—Julian W. Woo
(74) *Attorney, Agent, or Firm*—Fish & Richardson P.C.

(57) ABSTRACT

A tissue fastener comprises a shaft having a member disposed thereon for lodging the shaft within the tissue, the shaft having a region that is relatively flexible to render a tissue engaging head disposed at a proximal end of the shaft movable with respect to the shaft. In one embodiment, the region comprises substantially an entire length of the shaft and is made from flexible material, such as a mesh, onto which the member and the head are molded. In another embodiment, the shaft comprises generally rigid material, and the region comprises a flexible joint between the shaft and the head. The flexible joint comprises a breakable (e.g., frangible) section of the shaft, and a flexible member (e.g., a plurality of filaments or a flexible tube) extends between the shaft and the head past the breakable section.

35 Claims, 5 Drawing Sheets

U.S. PATENT DOCUMENTS

| | | | |
|---|---|---|---|
| 4,724,840 A | | 2/1988 | McVay et al. |
| 4,736,746 A | | 4/1988 | Anderson |
| 4,741,330 A | * | 5/1988 | Hayhurst et al. ............ 606/232 |
| 4,744,793 A | | 5/1988 | Parr et al. |
| 4,750,492 A | | 6/1988 | Jacobs |
| 4,772,286 A | | 9/1988 | Goble et al. |
| 4,790,850 A | | 12/1988 | Dunn et al. |
| 4,834,752 A | | 5/1989 | Van Kampen |
| 4,873,976 A | | 10/1989 | Schreiber |
| 4,884,572 A | | 12/1989 | Bays et al. |
| 4,895,148 A | | 1/1990 | Bays et al. |
| 4,917,554 A | | 4/1990 | Bronn |
| 4,924,865 A | | 5/1990 | Bays et al. |
| 4,940,467 A | | 7/1990 | Tronzo |
| 4,944,742 A | | 7/1990 | Clemow et al. |
| 4,950,285 A | | 8/1990 | Wilk |
| 4,969,892 A | | 11/1990 | Burton et al. |
| 4,976,715 A | | 12/1990 | Bays et al. |
| 5,013,316 A | | 5/1991 | Goble et al. |
| 5,053,047 A | | 10/1991 | Yoon |
| 5,059,206 A | | 10/1991 | Winters |
| 5,084,050 A | | 1/1992 | Draenert |
| 5,123,913 A | | 6/1992 | Wilk et al. |
| 5,147,362 A | | 9/1992 | Goble |
| 5,154,189 A | | 10/1992 | Oberlander |
| 5,167,665 A | | 12/1992 | McKinney |
| 5,246,441 A | | 9/1993 | Ross et al. |
| 5,258,015 A | | 11/1993 | Li et al. |
| 5,258,016 A | | 11/1993 | DiPoto et al. |
| 5,261,914 A | | 11/1993 | Warren |
| 5,269,783 A | * | 12/1993 | Sander ........................ 606/72 |
| 5,342,376 A | | 8/1994 | Ruff |
| 5,370,661 A | | 12/1994 | Branch |
| 5,382,257 A | * | 1/1995 | Lewis et al. .................. 606/72 |
| 5,382,259 A | * | 1/1995 | Phelps et al. ................ 606/151 |
| 5,425,747 A | | 6/1995 | Brotz |
| 5,425,766 A | * | 6/1995 | Bowald .................... 623/13.11 |
| 5,439,684 A | | 8/1995 | Prewett et al. |
| 5,490,750 A | | 2/1996 | Gundy |
| 5,496,326 A | | 3/1996 | Johnson |
| 5,500,000 A | * | 3/1996 | Feagin et al. ................ 606/232 |
| 5,507,812 A | | 4/1996 | Moore |
| 5,520,691 A | | 5/1996 | Branch |
| 5,562,704 A | | 10/1996 | Tamminmaki et al. |
| 5,569,252 A | | 10/1996 | Justin et al. |
| 5,569,303 A | | 10/1996 | Johnson |
| 5,569,306 A | | 10/1996 | Thal |
| 5,593,425 A | | 1/1997 | Bonutti et al. |
| 5,601,571 A | | 2/1997 | Moss |
| 5,628,766 A | | 5/1997 | Johnson |
| 5,641,256 A | | 6/1997 | Gundy |
| 5,643,320 A | | 7/1997 | Lower et al. |
| 5,662,683 A | | 9/1997 | Kay |
| 5,669,935 A | | 9/1997 | Rosenman et al. |
| 5,690,676 A | | 11/1997 | DiPoto et al. |
| 5,690,678 A | | 11/1997 | Johnson |
| 5,713,904 A | | 2/1998 | Errico et al. |
| 5,716,359 A | | 2/1998 | Ojima et al. |
| 5,720,765 A | | 2/1998 | Thal |
| 5,720,766 A | | 2/1998 | Zang et al. |
| 5,728,116 A | | 3/1998 | Rosenman |
| 5,728,136 A | | 3/1998 | Thal |
| 5,730,744 A | | 3/1998 | Justin et al. |
| 5,735,875 A | | 4/1998 | Bonutti et al. |
| 5,792,182 A | | 8/1998 | Johnson |
| 5,827,298 A | | 10/1998 | Hart et al. |
| 5,843,084 A | | 12/1998 | Hart et al. |
| 5,895,396 A | | 4/1999 | Day et al. |
| 5,921,986 A | | 7/1999 | Bonutti |
| 5,941,439 A | | 8/1999 | Kammerer et al. |
| 5,944,738 A | * | 8/1999 | Amplatz et al. ............. 606/213 |
| 5,964,783 A | | 10/1999 | Grafton et al. |
| 5,980,557 A | | 11/1999 | Iserin et al. |
| 5,984,927 A | | 11/1999 | Wenstrom, Jr. et al. |
| 5,993,475 A | | 11/1999 | Lin et al. |
| 6,036,701 A | | 3/2000 | Rosenman |
| 6,056,778 A | | 5/2000 | Grafton et al. |
| 6,096,060 A | | 8/2000 | Fitts et al. |
| 6,099,568 A | | 8/2000 | Simonian et al. |
| 6,146,387 A | | 11/2000 | Trott et al. |
| 6,152,935 A | | 11/2000 | Kammerer et al. |
| 6,156,044 A | | 12/2000 | Kammerer et al. |
| 6,179,840 B1 | | 1/2001 | Bowman |
| 6,203,572 B1 | | 3/2001 | Johnson et al. |

\* cited by examiner

TISSUE FASTENER

BACKGROUND

This invention relates to tissue fasteners, in particular to devices for attaching soft tissue (e.g., tendons, ligaments, or cartilage) to bone or to other soft tissue.

One conventional tissue fastener used to re-attach cartilage to bone comprises an elongated shaft with a series of barbs that enable the shaft to be inserted through tissue but resist withdrawal thereafter. The distal tip of the shaft is sharp, and the proximal end of the shaft terminates at an enlarged head. To re-attach soft tissue to bone, the fastener is pushed through the soft tissue into a pre-formed hole in the bone until the soft tissue is secured between the head and the bone surface. The barbs resist withdrawal from the hole, thereby holding the fastener (and thus the soft tissue) in place.

SUMMARY

One aspect of the invention features a tissue fastener comprising a shaft having a member disposed thereon for lodging the shaft within the tissue, the shaft having a region that is relatively flexible to render a tissue engaging head disposed at a proximal end of the shaft movable with respect to the shaft.

Preferred embodiments may include one or more of the following features.

In one embodiment, the region comprises substantially an entire length of the shaft. The region comprises flexible material, such as a mesh. The member and the head are molded onto the mesh. The member comprises at least one barb.

In another embodiment, the shaft comprises generally rigid material, and the region comprises a flexible joint between the shaft and the head. The flexible joint comprises a breakable section of the shaft. For example, the section is constructed to be frangible (i.e., readily broken). A flexible member extends between the shaft and the head past the breakable section. The flexible member comprises, e.g., a plurality of filaments or a flexible tube. The flexible member extends along substantially an entire length of the shaft. The breakable section is defined by at least one opening disposed through a wall of the shaft. The shaft and the head comprise an integral molded unit, and the flexible member is molded therewithin.

The tissue fastener is made from polymeric material, such as a bioabsorbable material. The shaft is hollow and defines an interior passage. The head includes an opening in communication with the passage. The passage may be open or closed at a distal end of the shaft.

In one embodiment, the head has a flat distal surface. In another approach, the head has a toothed distal surface.

Another aspect of the invention features the tissue fastener and an insertion tool engageable with the tissue fastener for inserting the tissue fastener into tissue.

Preferred embodiments may include one or more of the following features. The tissue fastener member is disposed at a distal region of the shaft for lodging the shaft within the tissue, and the tissue engaging head is disposed at a proximal end of the shaft, and the shaft is relatively flexible between the member and the head. The insertion tool has an engagement portion for engaging the member. The head includes an aperture, and the engagement portion of the tool is configured to extend through the aperture when engaged with the member.

Other aspects of the invention feature methods for tissue attachment using the tissue fastener. One such method comprises inserting the tissue fastener through a first tissue and into a second tissue so that the member lodges within the second tissue and the head urges the first tissue against the second tissue.

Preferred embodiments may include one or more of the following features.

The first tissue and the second tissue are regions of a common tissue structure. For example, the tissue is cartilage and, prior to the inserting, the first region is separated from the second region by a tear in the cartilage.

Alternatively, the first tissue is soft tissue and the second tissue is bone.

Another aspect of the invention features a method for making a tissue fastener comprising providing a shaft having a member disposed thereon for lodging the shaft within the tissue, and a tissue engaging head disposed at a proximal end of the shaft, and making a region of the shaft relatively flexible to render the head movable with respect to the shaft.

Preferred embodiments include making the tissue fastener so as to have the structural features discussed above.

The flexibility of the tissue fastener allows the head to move (either from side to side or up and down) in response to loads imposed by the tissue, without compromising the security of the tissue attachment. As a result, healing is promoted even in high stress applications, with little risk of the head digging into, and potentially damaging, the tissue. The tissue fastener is particularly (but by no means exclusively) useful in the treatment of shoulder and knee instability, and in small joint repairs. These applications include meniscal repair, rotator cuff repair, Bankhart procedures, and treatment of "slap" lesions.

Other features and advantages of the invention will become apparent from the following description, and from the claims.

DESCRIPTION OF EMBODIMENTS

Figure 1:
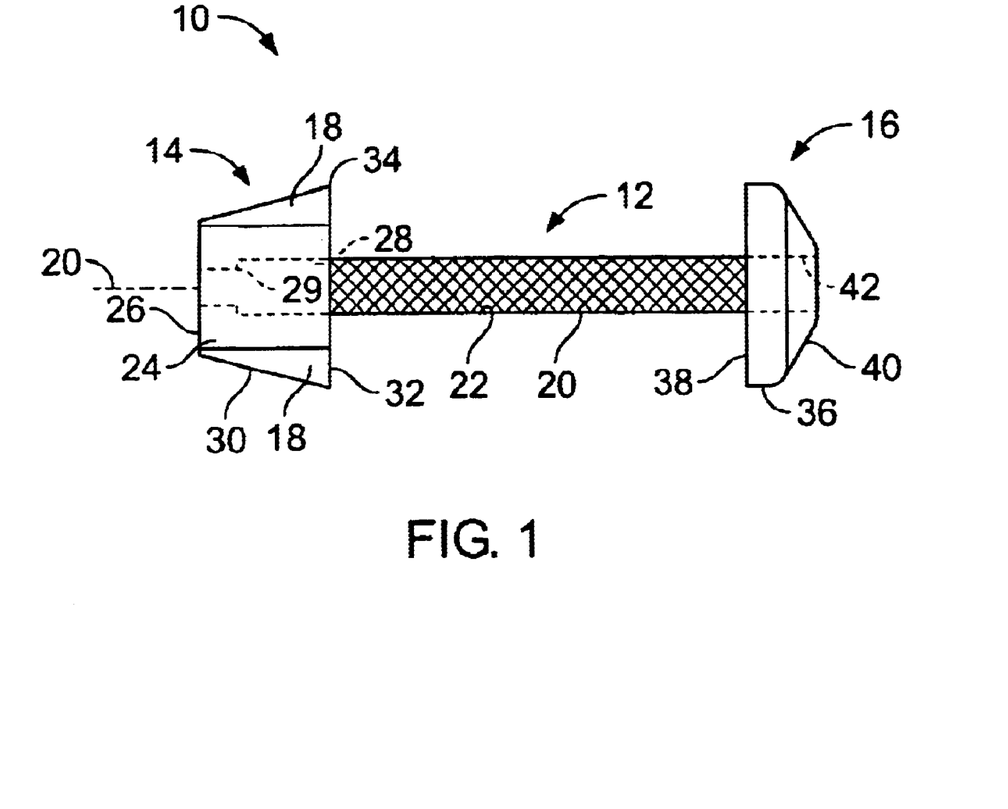
FIGS. 1 and 2 show a tissue fastener.
Figure 2:
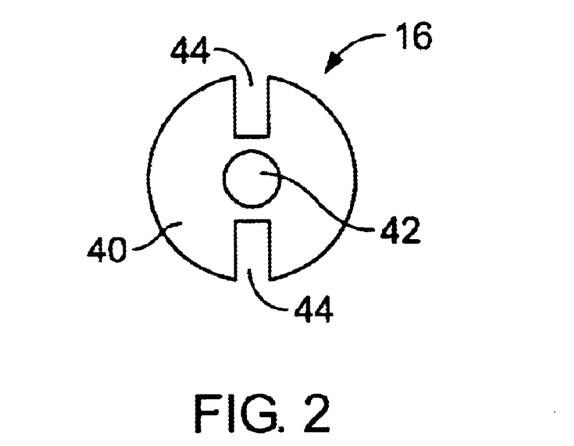

FIGS. 1 and 2 show one embodiment of a flexible tissue fastener 10 that includes a flexible shaft 12 and a generally rigid tip 14 and head 16 mounted at opposite ends of shaft 12. A pair of generally rigid barbs 18 extend from tip 14 for anchoring fastener in place within tissue. Shaft 12, tip 14, and head 16 are hollow and have open-ended passages which are in communication along a longitudinal axis 20 of fastener 10 for purposes to be described.

Shaft 12 comprises a woven polymeric mesh 20 made from a bioabsorbable polymer, preferably polylactic acid (PLA), that defines an interior passage 22 open at both its proximal and distal ends. The woven nature of mesh 20 renders shaft 12 flexible both transversely to and along longitudinal axis 20. Thus, when fastener 10 is in vivo, shaft 12 can flex from side to side with respect to axis 20 as the tissue applies shear forces to shaft 12 or head 16, thereby avoiding tearing of the tissue that might otherwise occur if shaft 12 was immobile. Additionally, shaft 12 can flex to allow head 18 to lie flush with the tissue after insertion in applications in which fastener 10 is not inserted perpendicularly to the tissue surface. Thus, fastener 10 is less obtrusive in vivo than rigid fasteners, and is less prone to damage either the tissue being fastened or surrounding tissue.

The woven nature of mesh 20 also makes shaft 12 radially compressible, allowing fastener 10 to be even less obtrusive when subject to compressive forces that may be encountered when fastener is used to attached soft tissue to other soft tissue. An example of such an application is the use of fastener 10 to repair meniscal tissue (i.e., cartilage) tears.

Mesh 20 further also provides structure and surface area for insert molding tip 14 and head 16—which are preferably made from polymeric material—onto shaft 12. Insert molding these features 14, 16 allows the polymeric material to melt around the fibers of the mesh and mechanically lock features 14, 16 to shaft 12 upon cooling. A bioabsorbable material such as PLA is preferred for tip 14 (as well as barbs 18) and head 16, because PLA has a uniform rate of absorbability. Features 14, 16 are further integrated with woven mesh 20 by melting them into as well as around mesh 20.

Tip 14 is generally cylindrical and has an outer surface 24 from which barbs 18 radially extend. Tip 14 terminates at a flat, annular distal surface 26 that defines an open end of a passage 28 which extends through tip 14 and communicates with the hollow interior 22 of shaft 12. Passage 28 is sized to receive a K-wire to assist in guiding fastener 10 to the correct location in the tissue during emplacement (described below).

Barbs 18 are circumferentially spaced by 180 degrees around tip exterior surface 24 (although two barbs 18 are shown, it will be appreciated that more or fewer barbs 18 may be used, and that barbs 18 may be unevenly spaced around tip 14). Each barb 18 has a flat, inclined exterior surface 30 that slopes outwardly as barb 18 extends proximally. Barb 18 terminates at a proximal surface 32 oriented generally perpendicularly to axis 20. The junction of surfaces 30, 32 defines a sharp edge 34 which lodges barb 18 within tissue during use, as will be explained.

Head 16 includes an annular body 36 having a flat, tissue-engaging underside 38 and a rounded upper surface 40. A passage 42 extends through body 36, is aligned with the hollow interior 13 of shaft 12 and tip passage 28, and is open at both ends for receiving the K-wire during insertion. A pair of diametrically opposed slots 44 extend through body 36 between underside 38 and upper surface 40 for purposes to be described.

Body 36 is relatively thin to provide fastener 10 with a low profile when the device in place in vivo. The outer diameter of body 36 is approximately the same as (or slightly larger than) the maximum radial dimension defined by barbs 18. Body 36 has a substantially larger outer diameter than shaft 12, thereby enabling head 16 to capture tissue beneath it in a tack-like fashion when fastener 10 is emplaced, as will be described. The corners of body 36 are rounded at underside 38 and upper surface 40 to avoid tissue damage when shaft 12 flexes from side to side in response to movement of the tissue being tacked down by head 16.

Fastener 10 is manufactured by insert molding. More specifically, a length of woven mesh 20 is cut to a specific length for fastener 10 and is inserted over a core pin. The injection mold then closes on the core pin and polymeric material is then molded onto and around woven mesh 20. Fastener 10 has an overall length of 0.100–0.500 inch (of which approximately 0.060–0.300 inch corresponds to the length of shaft 12 between tip 14 and head 16) and a maximum width (defined by barbs 18 and the diameter of head 16) of 0.040–0.300 inch.

Figure 3:
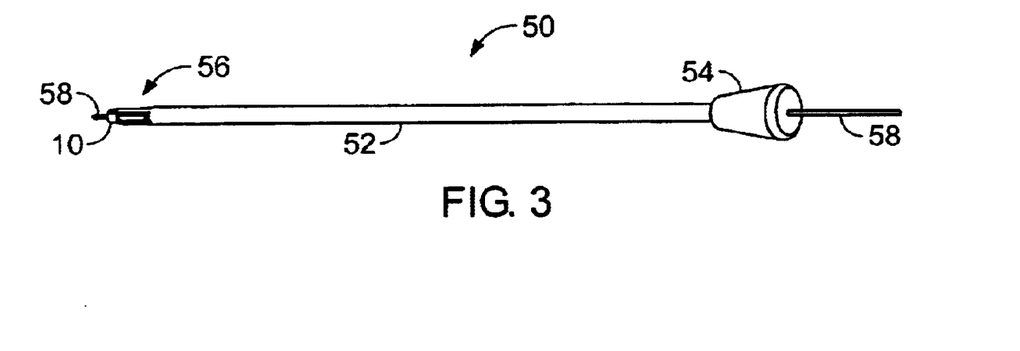
FIGS. 3–5 show the tissue fastener of FIG. 1 with an insertion tool.
Figure 4:
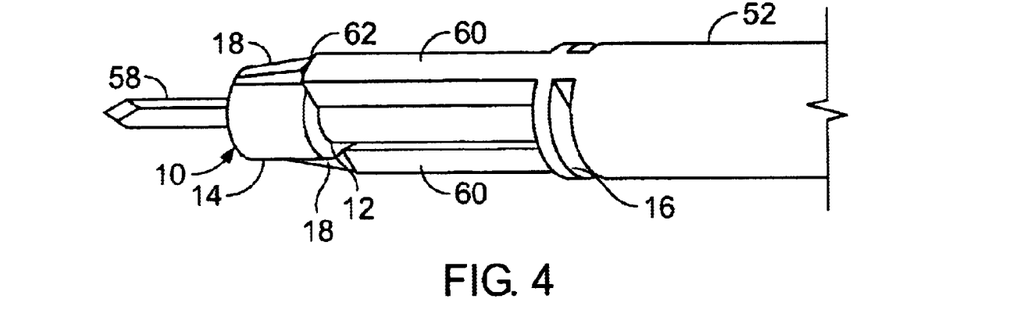
Figure 5:
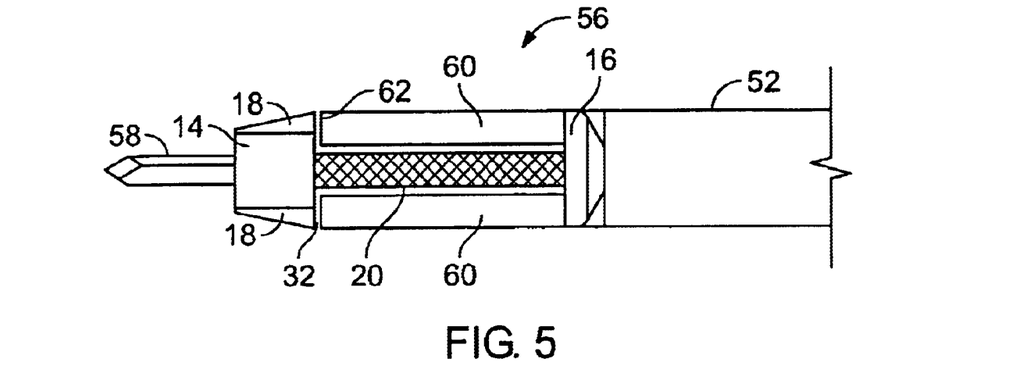

Referring also to FIGS. 3–5, an insertion tool 50 for emplacing fastener 10 in tissue includes a hollow, elongated rod 52 with a handle 54 at its proximal end and a fastener mount 56 at its distal end. Rod 52, handle 54, and mount 56 are hollow to accommodate a K-wire 58 used to guide a fastener 10 into place in the body. Rod 52 is sufficiently narrow to pass through a conventional cannula to the surgical site, and handle 54 is large enough to fit comfortably in the user's hand.

Mount 56 includes a pair of diametrically opposed arms 60 which extend from the distal end of rod 52. The circumferential spacing between arms 60 corresponds to that between barbs 18 and slots 44 in head 16. Arms 60 terminate at flat barb engaging surfaces 62. Fastener 10 is loaded onto insertion tool 50 by aligning slots 44 in head 16 with arms 60, and sliding fastener 10 proximally over arms 60 until surfaces 62 abut barb proximal surfaces 32.

Figure 6A:
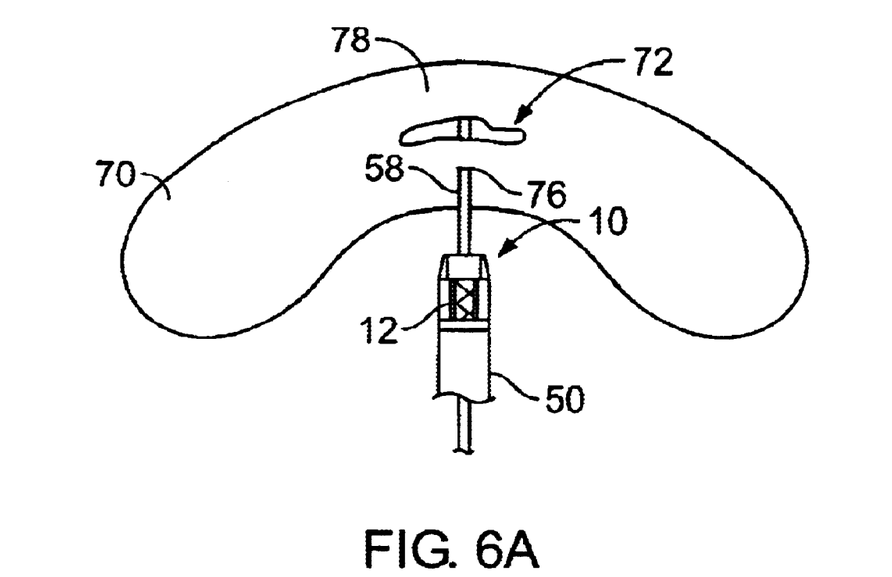
FIGS. 6A and 6B show the use of the tissue fastener of FIG. 1 to repair a tear in soft tissue.
Figure 6B:
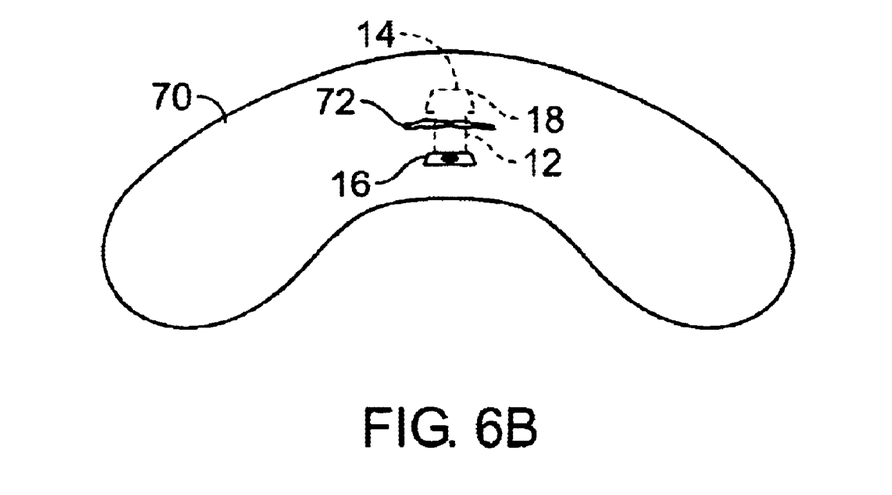

Referring to FIGS. 6A and 6B, in use, fastener 10 is used to repair torn meniscal tissue 70 (e.g., in the knee) as follows. As a first step in repairing tear 72, the surgeon determines the proper insertion site (or sites) 74 at which fastener 10 (or a plurality of fasteners 10) are to be emplaced. A relatively small tear 72 like that shown in FIGS. 6A and 6B may be repaired using only one fastener 10; multiple fasteners 10 may be needed to close larger tears. Insertion site 74 is located on the proximal side 76 of tear 72 (but the distal side of the tear may be used instead as the insertion site).

The surgeon then introduces K-wire 58 to the surgical site through a cannula (not shown), and stabs the tip of K-wire 58 into meniscal tissue at insertion site 74. The surgeon urges K-wire 58 distally until its tip spans tear 72 and becomes embedded in meniscal tissue 78 located distally of tear 72. Next, the surgeon attaches fastener 10 to mount 56 of insertion tool 50, as described above, slides the assembly over the proximal end of K-wire 58, and feeds the assembly over K-wire 58 to the surgical site.

Then, the surgeon holds K-wire 58 securely in place with one hand, and pushes insertion tool 50 distally with the other. The engagement between arms 60 and barbs 18, as well as the engagement of the distal end of rod 52 against head upper surface 40, pushes fastener 10 over K-wire 58. Fastener 10 thus enters insertion site 76 and passes through proximal meniscal tissue 76 and across tear 72. The sloped nature of barb surfaces 30 allow barbs 18 to smoothly pass through the meniscal tissue in the distal direction of movement.

The surgeon continues distally advancing fastener 10 to slide tip 15 further over K-wire 58 and into meniscal tissue 78 distally of tear 72. As fastener 10 moves distally, underside 38 of head 16 engages meniscal tissue 76 on the proximal side of the tear. The enlarged diameter of head 16 relative to shaft keeps head 16 from passing through the puncture behind shaft 12. As a result, head 16 urges proximal tissue 76 toward distal meniscal tissue 78 and gradually closes tear 72 as fastener 10 is advanced distally.

When barbs 18 have fully entered distal meniscal tissue 78, the tissue attempts to close against shaft 12. Thus, perpendicular barb surfaces 32 (FIG. 1) and edges 34 securely engage the meniscal tissue, and firmly lodge tip 14 in place therein. Tear 72 is now closed (FIG. 6B), and the surgeon withdraws insertion tool 50 and K-wire 58. With the meniscal tissue 76, 78 on the two sides of the tear held together by fastener 10, healing can begin. Over time, meniscal tissue 76, 78 will grow together, thereby permanently closing tear 72. In embodiments in which the materials of fastener 10 are biodegradable, fastener 10 gradually dissolves.

Figure 7A:
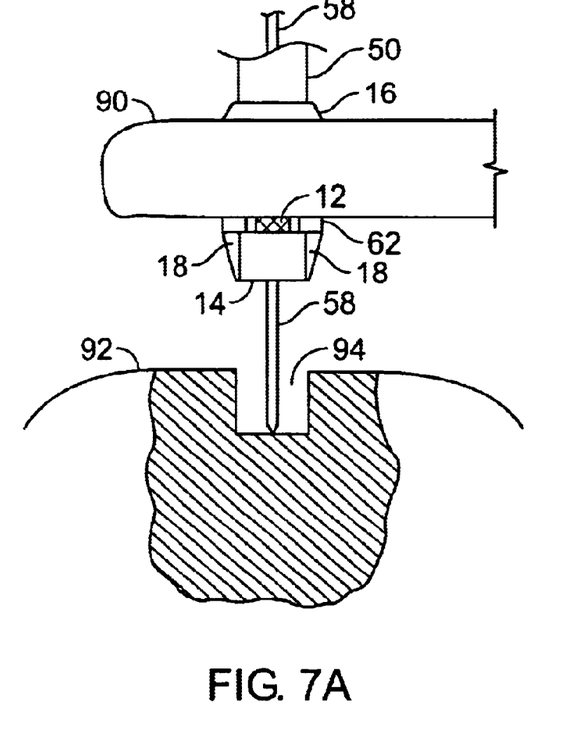
FIGS. 7A and 7B show the use of the tissue fastener of FIG. 1 to attach soft tissue to bone tissue.
Figure 7B:
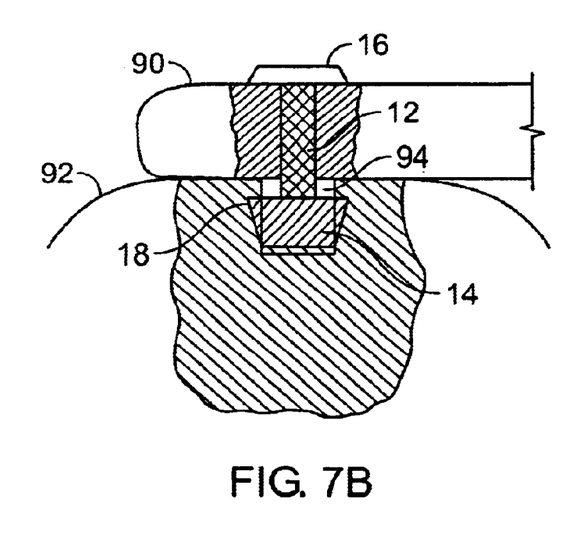

FIGS. 7A and 7B show the use of fastener 10 to reattach soft tissue 90 to bone 92 (e.g., during the repair of a torn rotator cuff). First, a hole 94 is formed in bone 92 at the desired attachment site, e.g., by drilling. K-wire 58 is introduced to the surgical site, punched through soft tissue 90 at the selected attachment location, and positioned in hole 94 to serve as a guide for fastener 10 and insertion tool 50. After fastener 10 is placed on insertion tool mount 56 as discussed above, the assembly is inserted over K-wire 58 and advanced to the surgical site. The surgeon holds K-wire 58 with one hand, and urges insertion tool 50 distally with the other, thereby punching fastener 10 through soft tissue 90 (FIG. 7A).

The surgeon continues to advance insertion tool 50 distally to insert fastener 10 into hole 94 (FIG. 7B). Barbs 18 lodge tip 14 securely within hole 9 by digging into the bone tissue (e.g., the cancellous bone) around hole 94. As fastener 10 moves into hole 94, underside 38 of fastener head 16 engages the upper surface of soft tissue 90, thereby urging the soft tissue toward and against the upper surface of bone 92. The enlarged nature of head 16 prevents fastener 10 from passing completely through soft tissue 90 and enabling fastener 10 to securely re-attach the tissue to the bone in a tack-like manner. When fastener 10 has been fully inserted into hole 94, the surgeon removes insertion tool 50 and K-wire 58.

Other embodiments are within the scope of the following claims.

For example, other materials may be used for mesh 20 and the generally rigid features (tip 14, head 16, and barbs 18). One alternative material is polyglycolic acid (PGA), which is a bioabsorbable material that degrades more rapidly in the body than PLA. The tissue fastener may alternatively be made from non-bioabsorbable material.

Barbs 18 may be located elsewhere on fastener 10, for example on shaft 12. Barbs 18 may be blunt, rather than sharp. Tip 14 may be tapered or beveled distally; tip 14 may have a sharpened distal edge to further facilitate insertion.

Other insertion tools may be employed. For example, the insertion tool may be configured to engage the interior of tip 14 (e.g., a shoulder 29, FIG. 1, formed in the walls that define the passage through tip 14). Alternatively, tip 14 may be solid.

Other kinds of flexible shafts are contemplated. Shaft 12 may comprise a braided or knitted mesh or comprise a non-mesh or non-polymeric material. Shaft 12 may be solid rather than defining a passage 22.

Shaft 12 may be rendered flexible in other ways. For example, a generally rigid tissue fastener may be modified to render it flexible at one or more places.

Figure 8:
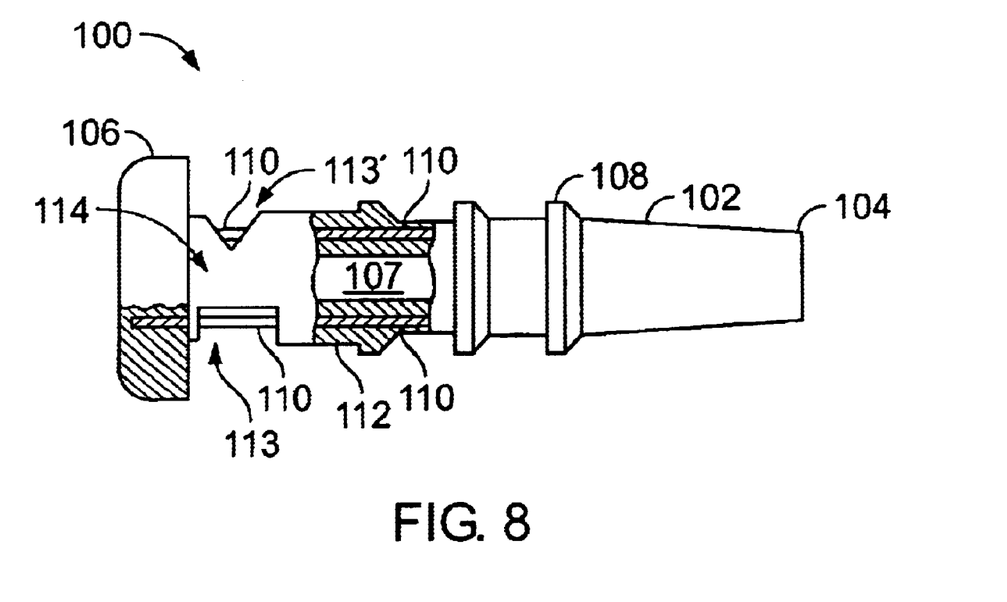
FIGS. 8 and 9 illustrate alternative embodiments of a tissue fastener.

FIG. 8 shows a fastener 100 that has been so modified. Fastener 100 is, e.g., a modified version of the Suretac™ fastener, manufactured by Smith & Nephew, Inc. and described in U.S. Pat. Nos. 5,100,417, 5,258,016, and 5,690, 676, all of which are incorporated herein by reference. Fastener 100 includes a hollow shaft 102 that extends proximally from a distal end 104 to a radially enlarged head 106. An interior passage 107 extends through shaft 102 and is open at distal end 104 and head 106. Fastener 100 is formed by molding so that shaft 102 and head 106 define an integral, unitary body.

A plurality of (e.g., three) axially spaced, circumferential ribs 108 are disposed on shaft between end 104 and head 106. Ribs 108 have beveled leading (i.e., distal) surfaces to facilitate advancement of fastener through tissue, and flat side and proximal surfaces that lodge within the tissue.

Fastener 100 made from polymeric material, such as the aforementioned PLA. During fabrication, flexible material 110 is embedded within the walls 112 of fastener 10, and shaft 102 is relieved to provide a breakable connection 114 between shaft 102 and head 106. Connection 114 is preferably frangible (i.e., easily breakable). This enables the rigid material of head 106 to break free from that of shaft 102 in response to side-loading imposed by the re-attached tissue, to reduce the risk of head 106 digging into or otherwise damaging the tissue. Flexible material 110 tethers head 106 to shaft 102, however, so that the tissue captured beneath head 106 remains securely attached to the tissue (e.g., bone tissue) into which shaft 102 has been inserted. In addition, flexible material 110 reinforces the walls of shaft 102.

Flexible material 110 may have a wide variety of configurations. For example, flexible material 110 may include individual strands of material (such as man-made or natural fibers or suture) or a flexible member such as a braided tube or braided mesh. Suitable materials include PLA, PGA, polyester, cat gut, polydioxanone, polypropylene, polyvinyl acetate, and natural materials such as wool, silk, and cotton.

Flexible material 110 is insert molded into shaft 102 and head 106 during the fabrication of fastener 10. Flexible material 110 preferably extends along the entire length of shaft 102, but alternatively may terminate proximally of end 104. Flexible material 110 is disposed uniformly around the circumference of shaft 102 and head 106, although flexible material 110 may alternatively be concentrated in, e.g., the segments of shaft 102 that are relieved. (Only one strand of flexible material 110 is shown on each side of shaft 102 for simplicity.)

Shaft 102 may be relieved in a variety of ways, only two of which—one or more rectangular holes 113 or one or more notches 113'—are shown. Shaft 102 may be relieved in as few or as many places as are suitable to provide the frangible connection. Preferably, shaft 102 is relieved in two diametrically opposed locations, and the same type of relief (e.g., openings such as holes 113 or notches 113') is used in each location. If insufficient relief is provided, frangible connection 114 may not break during use to achieve the desired flexibility. In contrast, care should be taken not to excessively relieve shaft 102, or frangible connection 114 may break during insertion of fastener 100 into tissue. As an alternative (or in addition) to openings 113, 113', shaft 102 may be relieved by making walls 112 relatively thin in the region of connection 114.

In use to, e.g., re-attach soft tissue to bone (the procedure shown in FIGS. 7A and 7B), fastener 110 is introduced to the surgical site over a K-wire, and an insertion tool (not shown) is advanced over the K-wire behind fastener 100. The insertion tool has a sufficient outer diameter to engage the upper surface of head 106 around the opening of passage 107. Thus, as the surgeon advances the insertion tool, he pushes shaft 102 through the soft tissue and into the bone hole. Ribs 108 engage against the sides of the bone hole to lodge fastener 100 in place, and head 106 captures the soft tissue against the upper surface of the bone.

Thereafter, when side loads are placed on the soft tissue (e.g., during movement by the patient), the side loads impose sufficient force to break frangible connections 114, thereby separating the rigid material of head 106 from that of shaft 102. Head 106 continues to press the soft tissue against the bone, however, due to the tethering provided by flexible material 100. The flexible connection of head 106 to shaft 102 acts as a hinge that allows head 106 to move from side to side (i.e., horizontally with respect to shaft 102) in response to further side loads. This avoids head 106 digging into, and perhaps damaging, the soft tissue.

Other embodiments of a tethered fastener are possible. For example, shaft 102 may be relieved after molding (such as by cutting holes 113 or notches 113').

Figure 9:
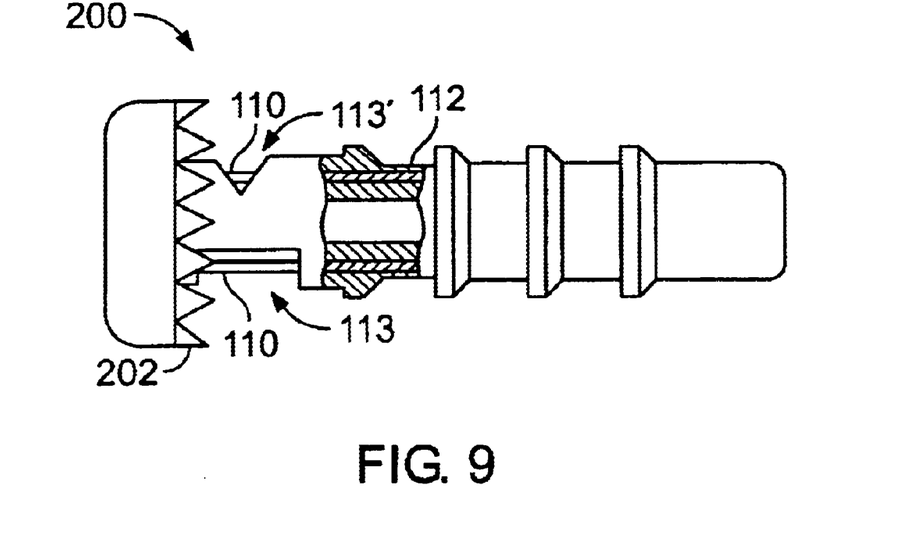

Referring to FIG. 9, fastener 200 is similar to fastener 100, except that teeth 202 protrude from the underside of the head for more secure tissue attachment. Flexible material 110 is insert molded within the walls of the shaft and head of fastener, and shaft is relieved with holes (113) or notches (113') to provide the frangible connection.

Still other embodiments are within the scope of the claims.

What is claimed is:

1. A tissue fastener comprising
    a generally rigid shaft having a member disposed thereon for lodging the shaft within the tissue,
    a tissue engaging head disposed at an end of the shaft, and
    a frangible section at least partially between the member and the head to render the head movable with respect to the shaft while maintaining the disposition of the head at the end of the shaft.
2. The tissue fastener of claim 1 wherein the member comprises at least one barb.
3. The tissue fastener of claim 1 wherein the fastener is made from polymeric material.
4. The tissue fastener of claim 1 wherein the fastener is made from bioabsorbable material.
5. The tissue fastener of claim 1 wherein the shaft is hollow and defines an interior passage, the head including an opening in communication with the passage.
6. The tissue fastener of claim 5 wherein the passage is open at a distal end of the shaft.
7. The tissue fastener of claim 5 wherein the passage is closed at a distal end of the shaft.
8. The tissue fastener of claim 1 wherein the head has a flat distal surface.
9. The tissue fastener of claim 1 wherein the head has a toothed distal surface.
10. The tissue fastener of claim 1 further comprising a flexible member extending between the shaft and the head past the frangible section.
11. The tissue fastener of claim 10 wherein the frangible section is defined by at least one opening disposed through a wall of the shaft.
12. The tissue fastener of claim 10 wherein the flexible member comprises a plurality of filaments.
13. The tissue fastener of claim 10 wherein the flexible member comprises a flexible tube.
14. A method for tissue attachment comprising
    providing a tissue fastener including a hollow shaft defining a substantially void interior passage and having an outer wall at least partially defining an exterior surface of the tissue fastener, the shaft having a member disposed thereon for lodging the shaft within soft tissue, and a tissue engaging head disposed at an end of the shaft, a region of the shaft being relatively flexible to render the head movable with respect to the shaft, and
    inserting the tissue fastener through a first tissue and into a second tissue so that the member lodges within the second tissue and the head urges the first tissue against the second tissue.
15. The method of claim 14 wherein the first tissue and the second tissue are regions of a common tissue structure.
16. The method of claim 15 wherein the tissue structure is cartilage and, prior to the inserting, the first region is separated from the second region by a tear in the cartilage.
17. The method of claim 14 wherein the first tissue is soft tissue and the second tissue is bone.
18. The method of claim 14 further comprising removably receiving an element in the interior passage during emplacement of the tissue fastener within soft tissue.
19. A method for making a tissue fastener comprising
    providing a generally rigid shaft having a member disposed thereon for lodging the shaft within the tissue, and a tissue engaging head disposed at an end of the shaft, and
    breaking the shaft to form a flexible region of the shaft to render the head movable with respect to the shaft.
20. The method of claim 19 further comprising providing a breakable section of the shaft, and extending a flexible member between the shaft and the head past the breakable section.
21. The method of claim 20 further comprising defining the breakable section by at least one opening disposed through a wall of the shaft.
22. The method of claim 20 wherein the flexible member comprises a plurality of filaments.
23. The method of claim 20 wherein the flexible member comprises a flexible tube.
24. The method of claim 20 further comprising extending the flexible member along substantially an entire length of the shaft.
25. The method of claim 20 further comprising molding the shaft and the head as an integral unit, and molding the flexible member therewithin.
26. The method of claim 19 further comprising making the tissue fastener from polymeric material.
27. The method of claim 19 further comprising making the tissue fastener from bioabsorbable material.
28. The method of claim 19 further comprising providing the shaft with an interior passage, and forming an opening in the head in communication with the passage.
29. The method of claim 28 further comprising opening the passage at a distal end of the shaft.
30. The method of claim 28 further comprising closing the passage at a distal end of the shaft.
31. The method of claim 19 further comprising providing the head with a flat distal surface.
32. The method of claim 19 further comprising providing the head with a toothed distal surface.
33. A tissue fastener comprising
    a generally rigid, hollow shaft defining a substantially void interior passage and having an outer wall at least partially defining an exterior surface of the tissue fastener, and
    a member disposed on the shaft for lodging the shaft within soft tissue, and
    a tissue engaging head disposed at an end of the shaft, the head including an opening in communication with the passage and having a maximum transverse cross-sectional length longer than the maximum transverse cross-sectional length of the hollow shaft,
    a region of the shaft being frangible to render the head movably connected to the rest of the shaft wherein the frangible region comprises a mesh.

34. A tissue fastener comprising
a hollow shaft defining a substantially void interior passage and having an outer wall at least partially defining an exterior surface of the tissue fastener, and
a member disposed on the shaft for lodging the shaft within soft tissue, and
a tissue engaging head disposed at an end of the shaft, the head including an opening in communication with the passage and having a maximum transverse cross-sectional length longer than the maximum transverse cross-sectional length of the hollow shaft,
a region of the shaft being relatively flexible to render the head movable with respect to the rest of the shaft,
wherein the member comprises a plurality of ribs.

35. A tissue fastener comprising a generally rigid, hollow shaft defining a substantially void interior passage and having an outer wall at least partially defining an exterior surface of the tissue fastener, and
a member disposed on the shaft for lodging the shaft within soft tissue, and
a tissue engaging head disposed at an end of the shaft, the head including an opening in communication with the passage and having a maximum transverse cross-sectional length longer than the maximum transverse cross-sectional length of the hollow shaft,
a region of the shaft being frangible to render the head movably connected to the rest of the shaft,
wherein the tissue fastener is made from bioabsorbable material.

* * * * *